US005482927A

United States Patent [19]

Maniar et al.

[11] Patent Number: 5,482,927
[45] Date of Patent: Jan. 9, 1996

[54] CONTROLLED RELEASED MICROPARTICULATE DELIVERY SYSTEM FOR PROTEINS

[75] Inventors: Manoj Maniar; Abraham J. Domb, both of Baltimore, Md.

[73] Assignee: Massachusetts Institute of Technology, Cambridge, Mass.

[21] Appl. No.: 200,370

[22] Filed: Feb. 23, 1994

Related U.S. Application Data

[63] Continuation of Ser. No. 658,089, Feb. 20, 1991, abandoned.
[51] Int. Cl.⁶ .............................. A61K 9/16; A61K 38/27
[52] U.S. Cl. ............................. 514/12; 424/499; 424/502; 514/2
[58] Field of Search .................................... 424/496, 499, 424/491, 502; 514/2.12

[56] References Cited

U.S. PATENT DOCUMENTS

| | | | |
|---|---|---|---|
| 4,816,568 | 3/1989 | Hamilton, Jr. et al. | 530/363 |
| 4,925,661 | 5/1990 | Huang | 424/85.91 |
| 4,963,368 | 10/1990 | Antrim et al. | 424/94.2 |
| 5,110,595 | 5/1992 | Wang | 514/3 |

FOREIGN PATENT DOCUMENTS

| | | |
|---|---|---|
| 0257915 | 3/1988 | European Pat. Off. . |
| 0257368 | 3/1988 | European Pat. Off. ....... A61K 37/00 |
| 0350246 | 1/1990 | European Pat. Off. . |

OTHER PUBLICATIONS

Wang, "Lipids as Excipient in Sustained Release Insulin Implants," International *Journal of Pharmaceutics*, 54, 223 (1989).

*Primary Examiner*—Jeffrey E. Russel
*Attorney, Agent, or Firm*—Arnall Golden & Gregory

[57] ABSTRACT

An improved surface erodible controlled release composition and the manufacturing thereof, for the continuous administration of biologically active proteins or peptide fragments, is described. The biologically active protein is dissolved in water or a suitable solvent, alone or in combination with stabilizing agents. The solution is either lyophilized or spray dried to obtain a free flowing powder. The powder is then sieved to obtain the desired average particle size. The free flowing powder of the protein or the stabilized protein is then incorporated into a biodegradable matrix formed of fatty acid anhydride, fatty acid and/or a salt thereof. Examples using growth hormone and bovine serum albumin demonstrate enhanced release, stability and controlled release properties for the fatty acid anhydride microparticular system.

18 Claims, No Drawings

CONTROLLED RELEASED MICROPARTICULATE DELIVERY SYSTEM FOR PROTEINS

This is a continuation application of application U.S. Ser. No. 07/658,089 filed on Feb. 20, 1991, now abandoned.

BACKGROUND OF THE INVENTION

The present invention is in the area of bioerodible controlled release systems or the delivery and administration of labile proteins and peptides.

The concept of using biodegradable matrix systems for the delivery of drugs and therapeutically active agents has been well developed and demonstrated to be clinically useful. A number of methods have been well established for the controlled release of low molecular weight compounds. However, the delivery of high molecular weight compounds, such as biologically active proteins and peptides has been difficult with the presently investigated hydrophilic or hydrophobic, non-polymeric or polymeric matrices.

Alternative methods or carriers for delivery which correct the deficiencies in these systems have been sought for years. Bioerodible polymeric matrices have shown promise in the development of improved delivery systems. Several polymers have been used, including poly(lactides) and their copolymers with glycolic acid, poly(orthoesters), ethylene vinyl acetate and poly(anhydrides). Ethylene vinyl acetate has worked well for the release of biologically active proteins, but is not practical because it is non-degradable. Poly(lactide/co-glycolide) has not shown much promise because there is a considerable amount of aggregation and denaturation of the protein within the matrix. Poly(anhydrides) and poly(orthoesters) release proteins or peptides, but the release rates and the duration of release obtained were not acceptable.

It would be particularly desirable to develop a microparticulate controlled release delivery system for controlled delivery of biologically active proteins. An example of a biologically active and useful protein that is most effective when delivered continuously over extended periods of time is growth hormone. Unfortunately, this protein frequently aggregates, denatures and loses activity, within the matrix or during the preparation of the delivery system, making it difficult to deliver on a continuous basis.

A controlled release polymer implant system that has been developed to deliver growth hormone is described in European Patent Application Publication No. 210 039B which discloses a sustained release microcapsule that contains the protein or peptide, an organic base substance as a drug retaining substance, and wherein the microcapsule wall is made of a polymer. This system has several drawbacks. For example, because the device is not biodegradable, the device must be removed after treatment. Furthermore, the polymer utilized to form the device is limited to those which do not bind to nor promote aggregation of the protein. This limitation in the choice of the polymer also limits the range, type and extent of release of active agent. Polymers which might otherwise be desirable for reasons of release kinetics and duration, specifically polymers that are more hydrophilic or hydrophobic in nature, cannot be used due to interactions with, or adverse influence upon, the biologically active protein. The device is also limited to subcutaneous implantation in animals since use in humans would require post treatment removal of the device.

It is therefore an object of the present invention to provide a biodegradable controlled release microparticulate, injectable delivery system for controlled in vivo administration of proteins such as growth hormone.

It is another object of the present invention to provide a method of manufacturing a microparticulate injectable delivery system.

It is yet another object of the present invention to provide a method and means for stabilizing proteins such as growth hormone in biodegradable drug delivery systems, as well as a method of manufacturing a microparticulate injectable delivery system capable of delivering stabilized protein in the biologically active form.

It is still a further object of the present invention to provide a method and means for modulating the rate of release of the parent or stabilized polypeptidic agents from the microparticulate drug delivery system.

SUMMARY OF THE INVENTION

An improved surface erodible controlled release composition and the manufacture thereof, for the continuous administration of biologically active proteins or peptide fragments, is described. The biologically active protein is dissolved in water or a suitable solvent, alone or in combination with stabilizing agents. The solution is either lyophilized or spray dried to obtain a free flowing powder. The powder is then sieved to obtain the desired average particle size. The free flowing powder of the protein or the stabilized protein is then incorporated into a biodegradable matrix formed of fatty acid anhydride, fatty acid and/or a salt thereof.

Examples using growth hormone and bovine serum albumin demonstrate the release, stability, and controlled release properties for the fatty acid anhydride microparticular system.

DETAILED DESCRIPTION OF THE INVENTION

Controlled release compositions suitable for use in continuously delivering biologically active protein, such as growth hormone and bovine serum albumin, and having enhanced stability with little or no loss of activity, are formed from fatty acid anhydrides microparticles. The biodegradable microparticulate controlled delivery system containing biologically active proteins is useful in a wide range of applications. For example, the controlled release system is useful for controlled and/or enhanced administration of bovine, porcine or human growth hormones to livestock for increased milk production in lactating females and increased growth in maturing animals, as well as administration of growth hormone in human patients.

Proteins

The system is described in detail using bioerodible, biocompatible controlled release microparticulate injectable delivery systems wherein the protein is bovine somatotropic hormone (rbSt) and bovine serum albumin (BSA). The growth hormone is representative of labile proteins which tend to aggregate and BSA is representative of high molecular weight proteins. However, any protein or peptide having therapeutic or biological activity can be used. The term "biologically active protein" refers to any therapeutically or biologically active protein, protein fragment, peptide, or analog thereof, unless otherwise stated, including proteins, active protein fragments and peptides which are naturally occurring, recombinantly engineered or synthetically produced and which may further undergo various modifications, such as additions to or deletions of amino acids or domains or by glycosylation.

Fatty Acid Anhydrides

The microparticulate carriers are composed of a relatively large amount of fatty acid anhydride monomers or dimers, fatty acid and/or salts thereof. The fatty acid anhydrides include, but not limited to, stearic anhydride, lauric anhydride, and palmitic anhydride. Similarly, fatty acids include, but not limited to, alkane-carboxylic acid, for example lauric acid and/or the salts thereof. The fatty acid anhydrides can be obtained from a variety of commercial sources, such as Aldrich Chemical Co.

Salts of fatty acids have hitherto been used only as a lubricant in an impact tabletting process, but they have never been used in the controlled delivery of biologically active proteins or peptides. Similarly, stearic acid has been used in controlled release preparations, but only for the preparation of granules intended for the oral solid dosage form.

Stabilizing Agents

In the preferred embodiment, a simple surfactant such as polysorbate™ 80 high pH is used both as a stabilizer, to hinder aggregation and to increase the thermal stability of the protein towards denaturation, and to modulate the release rate of the protein from the biodegradable microparticulate controlled delivery system. Other stabilizers include, but are not limited to, simple polysaccharides such as sucrose, deoxycholic acid, sodium sulfate, polysorbate 80 neutral pH, polyhydric alcohols, and potassium carbonate. Other protein stabilizing agents are known to those skilled in the art. The most preferred agent is sucrose or sodium sulfate.

The stabilizer causes a substantial increase in the duration of release of the protein and a decrease in initial release rate, when compared to a polymeric matrix formed from a biodegradable polymer in the absence of stabilizer, which permits longer and more uniform therapeutic treatment, without aggregation of the protein. The stabilizing agent has several other effects on the protein. It stabilizes and protects the protein from denaturation, degradation and aggregation, thereby enhancing in vivo activity and allowing longer treatment periods between the successive injections. Co-lyophilization or spray drying the solution of protein with the stabilizer also alters both the rate of release and duration of release of the growth hormone from the microparticulate matrix. Significant control of the release rate and the released biological activity is achieved by this combination of stabilizer, protein, and microparticulate carriers.

Method of Preparation

The preferred method of making a controlled release, bioerodible, biocompatible, microparticulate injectable delivery system for the controlled delivery of biologically active protein is as follows.

The biologically active protein is dissolved in an appropriate solvent, such as water. The solution is then lyophilized or spray dried to obtain a free flowing powder. Stabilized protein is obtained by co-lyophilizing or spray drying an aqueous solution of the growth hormone and the stabilizer. The free flowing powder is further reduced in particle size by mild trituration in a mortar with pestle. The powder is then sieved to obtain the desired particle size, ranging generally from 10 to 400μ, most preferably approximately 100μ for subcutaneous administration. The protein powder is then melt mixed with the appropriate microparticulate carrier, such as fatty acid anhydride or fatty acid and/or salts thereof. The fatty acid anhydride is selected based on the denaturation temperature of the protein to be delivered. The resulting melt is solidified by cooling to room temperature and then powdered to the desired particle size, in the range of 100 to 500μ, using any of the particle size reducing equipment known to those skilled in the art. In general, the ratio of protein to fatty acid anhydride will be in the range of 1% to 50%. When stabilizer is added, it will generally be in the range from 5 to 100% of the amount of protein.

Alternatively, the powdered and sieved protein is suspended in a solution of the microparticulate carrier. The suspension is spray dried to obtain the final product. The spray dried mixture can be used as an injectable or could be compressed into a device of specific shape for use as an implantable delivery system.

In yet another process, the sieved powder can be dry mixed with the appropriate microparticulate carrier, at the desired loading ratio, and processed by microencapsulation or pressing into an implantable device. The microparticulate product or the devices are preferably stored at −20° C. under an inert atmosphere prior to use.

Carriers for in vivo Administration

Prolonged in vivo activity can be achieved by selecting an appropriate vehicle for suspending and administering the microparticles. The preferred vehicles are the vegetable and/or mineral oils, mono, di or triglycerides like miglyols, and/or any fats and waxes of natural or synthetic origin which are deemed suitable as biocompatible materials.

The present invention is further described with reference to the following non-limiting examples demonstrating the preparation and characterization of microparticles with varying loading.

Example 1: Preparation of microparticles of stearic acid containing recombinant bovine somatotropin (rbSt) by melt mixing Microparticles of stearic acid were prepared by combining the spray dried rbSt (20 mg) with stearic acid (80 mg). Spray dried powdered rbSt was added to the stearic acid, which was pre-melted at 75° C. The melt dispersion was mixed thoroughly with a spatula and cast into a thin film. The thin film was then grounded into the particles of the desired average size, approximately 400μ.

Example 2: Preparation of microparticles of stearic anhydride containing rbSt by solvent method A 2% solution (4 ml) of stearic anhydride was prepared by dissolving the stearic anhydride in dichloromethane. Powdered rbSt (20 mg) was added to that solution and a uniform dispersion was obtained by vortexing the suspension. The suspension was cast as a thin film on a glass plate. The solvent was removed from the film using a stream of dry nitrogen gas. After removal of the solvent, particles of stearic anhydride embedded with rbSt were obtained. Residual solvent was completely removed by lyophilizing the particles.

The solvent free particles were powdered into a desired size range for in vivo application, approximately 400μ.

Example 3: Preparation of microparticles of stearic anhydride containing rbSt by spray drying method A suspension of rbSt in a solution of stearic anhydride was prepared as described in Example 2. The suspension was spray dried in a Buchi spray dryer to obtain microparticles embedded with rbSt. The average particle size of the microparticles was less than 250 microns.

Example 4: Preparation of microparticles of lauric acid containing bovine serum albumin (BSA) by melt mixing Microparticles of stearic acid were prepared by combining the spray dried BSA (20 mg) with lauric acid (80 mg). Spray dried powdered rbSt was added to the lauric acid, which was pre-melted at 45° C. The melt dispersion was mixed thoroughly with a spatula and cast into a thin film. The thin film was then grounded into the particles of the desired average size, approximately 400μ.

Example 5: Preparation of stabilized rbSt

The rbSt (150 mg) and stabilizer (37 mg) were dissolved in 200 ml of highly purified water. The solution is then transferred to a lyophilization flask. The solution is pre-frozen using a dry ice/acetone bath and lyophilized by standard methods. The resulting white crystalline powder is then reduced to the desired particle size by triturating it in a mortar with pestle. The stabilizers evaluated were sucrose, potassium carbonate, sodium sulfate, deoxycholic acid and polysorbate 80. In case of polysorbate 80, the amount of rbSt and stabilizer were 100 mg and 5 mg, respectively.

Example 6: Preparation of microparticles of stearic anhydride containing stabilized rbSt Microparticles of stearic anhydride were prepared by combining the stabilized rbSt (75 mg), as described in Example 5, with stearic anhydride (300 mg) to obtain 20% w/w loading. Stabilized rbSt was added to the stearic anhydride, which was pre-melted at 75° C. The melt dispersion was mixed thoroughly with a spatula and cast into a thin film. The thin film was then ground into particles of the desired average size. When the rbst was stabilized with polysorbate 80, the amount of stabilized rbSt and stearic anhydride were 50 mg and 200 mg, respectively.

Example 7: Preparation of microparticles of palmitic acid and palmitic anhydride containing rbSt Microparticles of palmitic acid and palmitic anhydride were prepared by combining spray dried rbSt (75 mg) with palmitic acid (225 mg) and palmitic anhydride (225 mg), respectively. Spray dried powdered rbSt was added to the palmitic acid and palmitic anhydride, which were pre-melted at 65° C. The melt dispersion was mixed thoroughly with a spatula and cast into a thin film. The thin film was then ground into the particles of the desired average size.

Example 8: Release of spray dried rbSt from the microparticles of palmitic acid and palmitic anhydride Release studies were conducted with the microparticles (125 mg) of palmitic acid and palmitic anhydride containing spray dried rbSt prepared in example 7 by dispersing them in 20 ml of 0.1M phosphate buffer, pH 7.4. The release study was conducted at 25° C. and the entire buffer was changed at appropriate time intervals. The amount of rbSt released was analyzed by size exclusion high pressure liquid chromatography. The release profile indicated that almost 80% of the rbST from palmitic anhydride, and almost 60% of the rbST from the palmitio acid, was released in an even fashion over approximately 150 hours.

Example 9: Release of spray dried rbSt from the microparticles of stearic acid and stearic anhydride Release studies were conducted with the microparticles (125 mg) of stearic acid and stearic anhydride containing spray dried rbSt prepared in example 1 and 3 by dispersing them in 20 ml of 0.1M phosphate buffer, pH 7.4. The release study was conducted at 25° C. and the entire buffer was changed at appropriate time intervals. The amount of rbSt released was analyzed by size exclusion chromatography. The release profile indicated that approximately 80% of the rbST was released from both types of microparticles after 100 hours.

Example 10: Release of stabilized rbSt from the microparticles of stearic anhydride Release studies were conducted with the microparticles (125 mg) of stearic anhydride containing stabilized rbSt prepared as described in Example 6 by dispersing them in 20 ml of 0.1M phosphate buffer, pH 7.4. The release study was conducted at 37° C. and the entire buffer was changed at appropriate time intervals. The amount of rbSt released was analyzed by size exclusion chromatography. The release profile indicates that over 80% of the stabilized rbST was released from the Polysorbate™80 High pH sucrose, and potassium carbonate microparticles after 80 hours, and that over 40% of the rbST from the sucrose stabilized microcapsule was released after 50 hours.

Example 11: Release of BSA from the microparticles of lauric acid

Release studies were conducted with the microparticles (125 mg) of lauric acid containing spray dried BSA prepared as described in Example 4 by dispersing them in 20 ml of 0.1M phosphate buffer, pH 7.4. The release study was conducted at 25° C. and the entire buffer was changed at appropriate time intervals. The amount of BSA released was analyzed by size exclusion chromatography. The release profile indicated that over 80% of the BSA was released in 100 hours.

The results in the above examples demonstrate that proteins can be incorporated into a microparticulate injectable system formed of fatty acids and fatty acid anhydrides for delivery of biologically active proteins, based on molecular weight determinations of the active monomer (versus the inactive dimer) and by radioimmunoassay. The combination of stabilizer and surface eroding matrix results in more complete release of the protein over an extended period of time. The highest yield and most linear results were obtained by the use of stearic anhydride and lauric acid.

Modifications and variations of the fatty acid microparticles for controlled release of proteins will be obvious to those skilled in the art, and are intended to come within the scope of the appended claims.

We claim:

1. A solid injectable microparticle consisting essentially of at least one fatty acid anhydride dimer, or at least one fatty acid and at least one fatty acid anhydride dimer, having dispersed within the microparticle a substance selected from the group consisting of a biologically active protein and a peptide.

2. The microparticle of claim 1 wherein the ratio of substance to fatty acid anhydride is in the range of 1:100 to 1:2, by weight of the substance to fatty acid anhydride.

3. The microparticle of claim 1 wherein the substance is dispersed in combination with a stabilizer.

4. The microparticle of claim 3 wherein the ratio of stabilizer to substance is in the range of 1:20 to 1:1, by weight of stabilizer to substance.

5. The microparticle of claim 1 wherein the substance is selected from the group consisting of biologically active proteins, protein fragments, and peptides, which are naturally occurring or recombinantly engineered.

6. The microparticle of claim 5 wherein the substance is growth hormone.

7. The microparticle of claim 1 wherein the fatty acid is selected from the group consisting of alkane-carboxylic acids and the fatty acid anhydrides are selected from the group consisting of stearic anhydride, lauric anhydride, palmitic anhydride, and other alkane-carboxylic anhydrides.

8. The microparticle of claim 1 having a size range of approximately 100 to 500 microns.

9. The microparticle of claim 1 further comprising a pharmaceutically acceptable carrier for administration to a human or an animal.

10. The microparticle of claim 9 wherein the carrier is selected from the group consisting of vegetable oils, mineral oils, and fats and waxes of natural or synthetic origin.

11. A method for the preparation of solid injectable microparticles for the controlled delivery of a substance selected from the group consisting of a biologically active protein and a peptide comprising incorporating the substance into solid injectable microparticles consisting essentially of fatty acid anhydride monomers or dimers, a mixture thereof, fatty acid and fatty acid anhydride monomers or dimers, or mixtures thereof, by the steps of:

providing the substance as a dry powder;

mixing the substance with melted fatty acid anhydride or a mixture of fatty acid and fatty acid anhydride at a temperature below which the substance denatures; and then solidifying the melted mixture to form the solid injectable microparticles.

12. The method of claim 11 wherein the ratio of substance to fatty acid anhydride is in the range of 1:100 to 1:2, by weight of the substance to fatty acid anhydride.

13. The method of claim 11 further comprising providing a stabilizer with the substance.

14. The method of claim 13 wherein the ratio of stabilizer to substance is in the range of 1:20 to 1:1, by weight of the stabilizer to substance.

15. The method of claim 11 further comprising suspending the microparticles in a pharmaceutically acceptable carrier for administration to a human or an animal wherein the pharmaceutically acceptable carrier is selected from the group consisting of vegetable oils, mineral oils, and fats and waxes of natural or synthetic origin, wherein the microparticles are suspended after the melted mixture is solidified.

16. The method of claim 11 wherein the substance is selected from the group consisting of biologically active proteins, protein fragments, and peptides, which are naturally occurring or recombinantly engineered.

17. The method of claim 16 wherein the substance is growth hormone.

18. A method for controlled delivery of a biologically active protein or peptide comprising administering solid injectable microparticles consisting essentially of fatty acid anhydride dimers, or a fatty acid and fatty acid anhydride dimers, having dispersed within the microparticles the biologically active protein or peptide, to a human or an animal in need of treatment with the protein or peptide in the microparticles.

* * * * *